(12) United States Patent
Jenkins et al.

(10) Patent No.: US 7,697,974 B2
(45) Date of Patent: Apr. 13, 2010

(54) METHODS AND APPARATUS FOR ANALYSIS OF ANGIOGRAPHIC AND OTHER CYCLICAL IMAGES

(75) Inventors: John H. Jenkins, Grand Prairie, TX (US); Mark D. Palma, Fitchburg, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1175 days.

(21) Appl. No.: 10/684,107

(22) Filed: Oct. 10, 2003

(65) Prior Publication Data

US 2005/0080327 A1 Apr. 14, 2005

(51) Int. Cl.
*A61B 5/05* (2006.01)
(52) U.S. Cl. .............................. 600/428; 378/8; 378/21; 600/407; 600/413; 600/410; 600/509; 382/128
(58) Field of Classification Search ......... 600/407–410, 600/428, 509, 413; 378/4, 21, 8; 382/128
See application file for complete search history.

(56) References Cited

U.S. PATENT DOCUMENTS 5,860,927 A   1/1999 Sakaguchi et al.
6,409,659 B1   6/2002 Warner et al.
6,501,979 B1 * 12/2002 Manning et al. ............ 600/413
7,314,446 B2 *  1/2008 Byrd et al. .................. 600/443
2002/0082850 A1   6/2002 Panelli
2004/0092816 A1 *  5/2004 Ossmann et al. ............ 600/428

OTHER PUBLICATIONS

"ECG-Based Selection of Angiographic Images using DICOM Facilities" J. Christiaens et al., Computers in Cardiology, 1999, pp. 447-45.*
"The Development of an Application Profile for DICOM Waveforms in the Cathlab" T. Becker et al., Computer in Cardiology, 1999, pp. 97-99.*

* cited by examiner

*Primary Examiner*—Brian Casler
*Assistant Examiner*—John F Ramirez
(74) *Attorney, Agent, or Firm*—Armstrong Teasdale LLP (57) ABSTRACT

A method for analyzing stored frames of time-stamped imaging data and time-stamped physiologic data obtained during a study of a patient during a plurality of cardiac cycles. The imaging data includes frames representative of a succession of images of the patient's heart. These configurations use a computer to analyze the stored physiologic data to determine times of a selected phase in the plurality of cardiac cycles, select, in the plurality of cardiac cycles, stored images corresponding to the determined times of the selected phase, and align and average images corresponding to the selected phase across the plurality of cardiac cycles to produce a single representative frame of image data.

23 Claims, 5 Drawing Sheets

METHODS AND APPARATUS FOR ANALYSIS OF ANGIOGRAPHIC AND OTHER CYCLICAL IMAGES

BACKGROUND OF THE INVENTION

This invention relates generally to methods and apparatus for diagnostic medical imaging and more particularly to methods and apparatus for automated angiographic analysis. However, the invention is also more generally useful for analysis of other cyclical images.

A coronary angiogram (or synonymously, an arteriogram) is an x-ray of the coronary arteries. Such images help the physician observe blocked arteries for the diagnosis of coronary artery disease. An angiogram is often part of a cardiac catheterization procedure including other tests and measurements. A patient undergoing catheterization also undergoes physiological monitoring. Typically, an electrocardiogram (ECG or, synonymously, EKG) is produced from electrical leads attached to a patient and analyzed to detect irregularities indicative of heart damage or disease. Data from the ECG is stored in a computer database.

To perform an angiogram, a physician injects a contrast medium into the coronary arteries using catheter inserted through a blood vessel (such as a femoral artery) up to the heart and then takes an X-ray of the heart. The angiogram assists the physician in determining the location and severity of coronary artery disease. This information is then used to determine what, if any, treatment is medically appropriate.

Cardiac angiography is performed in a cardiac catheterization laboratory utilizing cardiovascular X-ray imaging equipment. Left ventricular analysis, which is the contour detection of the diastolic and systolic left ventricle, can be carried out by capturing images in which a contrast medium has been injected into the left ventricle.

Images produced by X-ray imaging equipment can be stored on photographic film or electronically as digital images. Typically, digital images are stored in DICOM (Digital Imaging and Communications in Medicine format) and stored and viewed at a workstation.

Cardiac angiography images are usually reviewed as moving pictures. For left ventricular analysis, the perimeter of the dye filled left ventricular chamber is manually or semi-automatically delineated in each portion of the cardiac cycle. Various known analysis methods require a user to manually select a pair of images, more particularly, a diastole and a systole image, draw or mark the contours of the dye filled ventricle. Automatic (i.e., computerized) edge detection is possible, but is often difficult due to lack of edge definition or obscuration by musculature inside the ventricle. More often than not, automated edge detection systems require manual adjustment for successful edge detection for left ventricular analysis.

BRIEF DESCRIPTION OF THE INVENTION

Some configurations of the present invention therefore provide a method for analyzing stored frames of time-stamped imaging data and time-stamped physiologic data obtained during a study of a patient during a plurality of cardiac cycles. The imaging data includes frames representative of a succession of images of the patient's heart. These configurations use a computer to analyze the stored physiologic data to determine times of a selected phase in the plurality of cardiac cycles, select, in the plurality of cardiac cycles, stored images corresponding to the determined times of the selected phase, and align and average images corresponding to the selected phase across the plurality of cardiac cycles to produce a single representative frame of image data.

Some configurations of the present invention provide a cardiology analysis apparatus for analyzing stored frames of time-stamped imaging data and time-stamped physiologic data obtained during a study of a patient during a plurality of cardiac cycles. The imaging data includes frames representative of a succession of images of the patient's heart. In the apparatus, a computer is configured to analyze the stored physiologic data to determine times of a selected phase in the plurality of cardiac cycles, select, in the plurality of cardiac cycles, stored images corresponding to the determined times of the selected phase, and align and average images corresponding to the selected phase across the plurality of cardiac cycles to produce a single representative frame of image data.

Still other configurations of the present invention provide a method for analyzing stored frames of time-stamped cyclical image data obtained during a study of an object during a plurality of cycles. The method uses a computer to analyze the stored time-stamped cyclical image data to determine time of a selected phase of the cycle, select, in the plurality of cycles of time-stamped cyclical image data, stored images corresponding to the determined times of the selected phase, and align and average images corresponding to the selected phase across the plurality of cycles to produce a single representative frame of image data.

Still other configurations of the present invention provide an analysis apparatus for analyzing stored frames of time-stamped cyclical imaging data and time-stamped waveform data obtained during a study of an object during a plurality of cycles. The imaging data includes frames representative of a succession of images of the object. The apparatus includes a computer that is configured to analyze the stored waveform data to determine times of a selected phase in the plurality of cycles, select, in the plurality of cycles, stored images corresponding to the determined times of the selected phase, and align and average images corresponding to the selected phase across the plurality of cycles to produce a single representative frame of image data.

It will be appreciated that configurations of the present invention directed to cardiac image analysis provide fully automatic left ventricle analysis using multiple images of systole and diastole. Using these multiple images, a single representative image of each phase proves more accurate and repeatable edge detection and dependent measures, such as ejection fraction than is known in current methods and apparatus. Corresponding advantages can be obtained in configurations of the present invention directed to other imaging applications, including non-medical applications in which various forms of cyclical data and images of an object are recorded.

DETAILED DESCRIPTION OF THE INVENTION

A technical effect of the systems and processes described herein include at least one of producing a single representative frame of image data from a plurality of stored images, providing left ventricle analysis using multiple images of systole and diastol, and facilitating measurement of ejection fraction.

Figure 1:
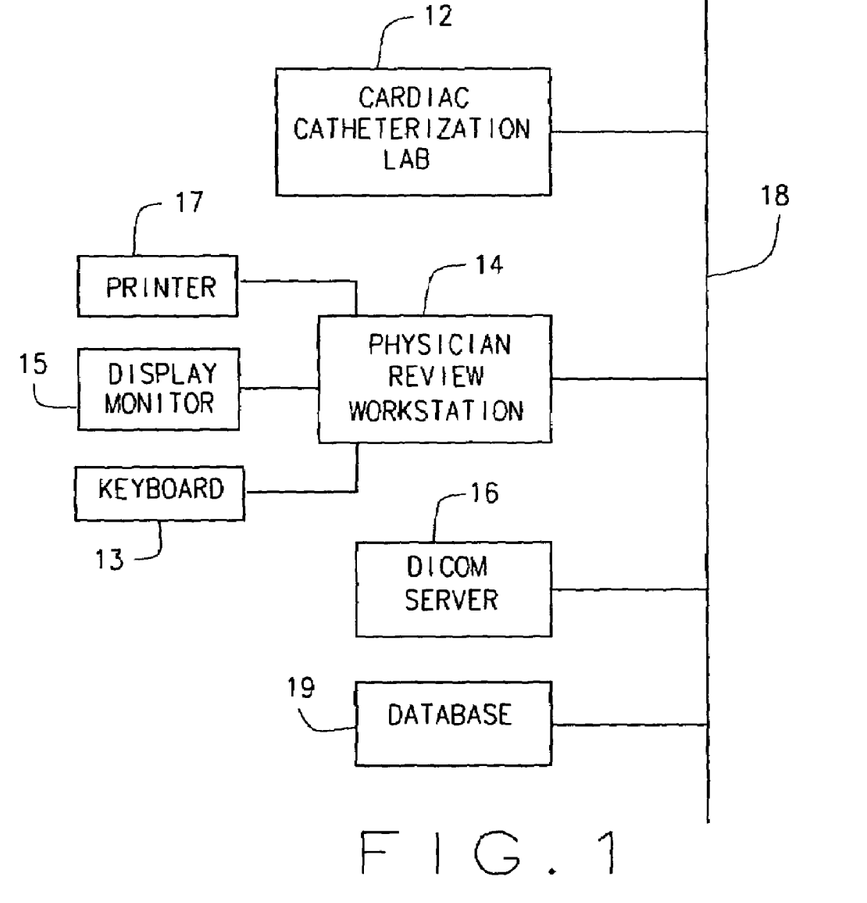
FIG. 1 is a block diagram depicting a network for facilitating storage and review of data acquired in a cardiac catheterization laboratory.

In some configurations of the present invention and referring to FIG. 1, a local area network (LAN) 18 facilitates communication between a systems housed in a cardiac catheterization laboratory 12, a physician review or overview workstation 14 and a DICOM server 16. For example, angiographic x-ray images acquired by imaging equipment in laboratory 12 and formatted as DICOM objects are transmitted by LAN 18 to a database 19 accessed by DICOM server 16. Workstation 14 can be used by a physician to display and perform quantitative analysis on retrieved images. Certain analysis, including left ventricular analysis, require the selection of images corresponding to particular cardiac events (e.g., systole and diastole). Workstation 14, in many configurations, is a computer that is part or all of a cardiology analysis apparatus. The cardiology analysis apparatus may further comprise an operator interface 13, such as a mouse and/or a keyboard, and a display monitor 15 and/or printer 17.

Figure 2:
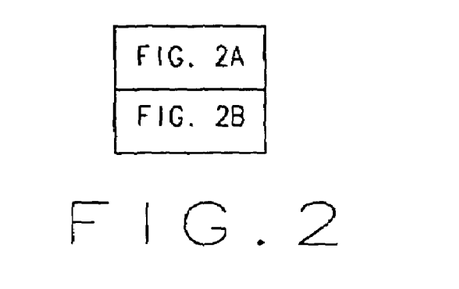
FIG. 2 is a block diagram depicting a cardiac catheterization laboratory networked to an asynchronous DICOM server with NTP time synchronization server.
Figure 2A:
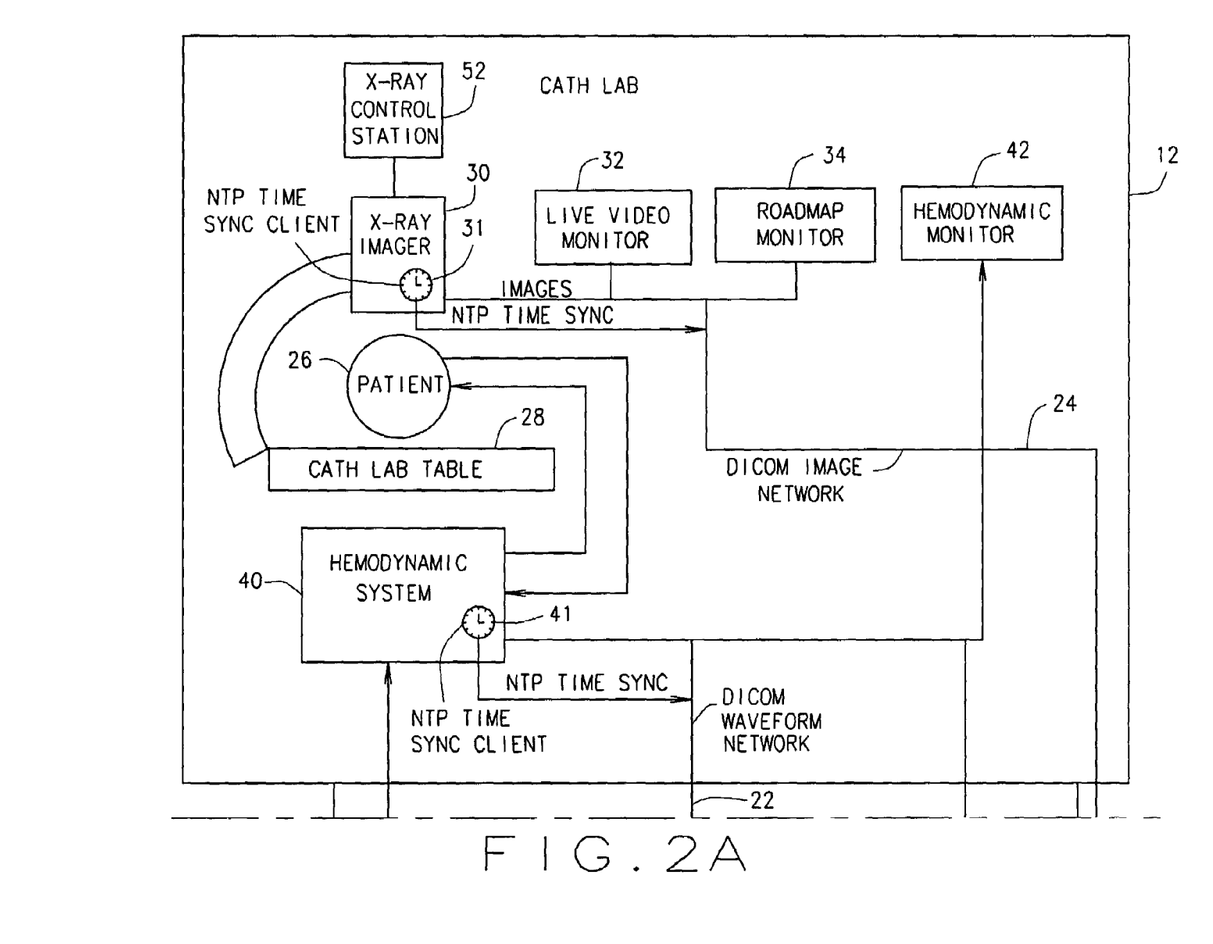
Figure 2B:
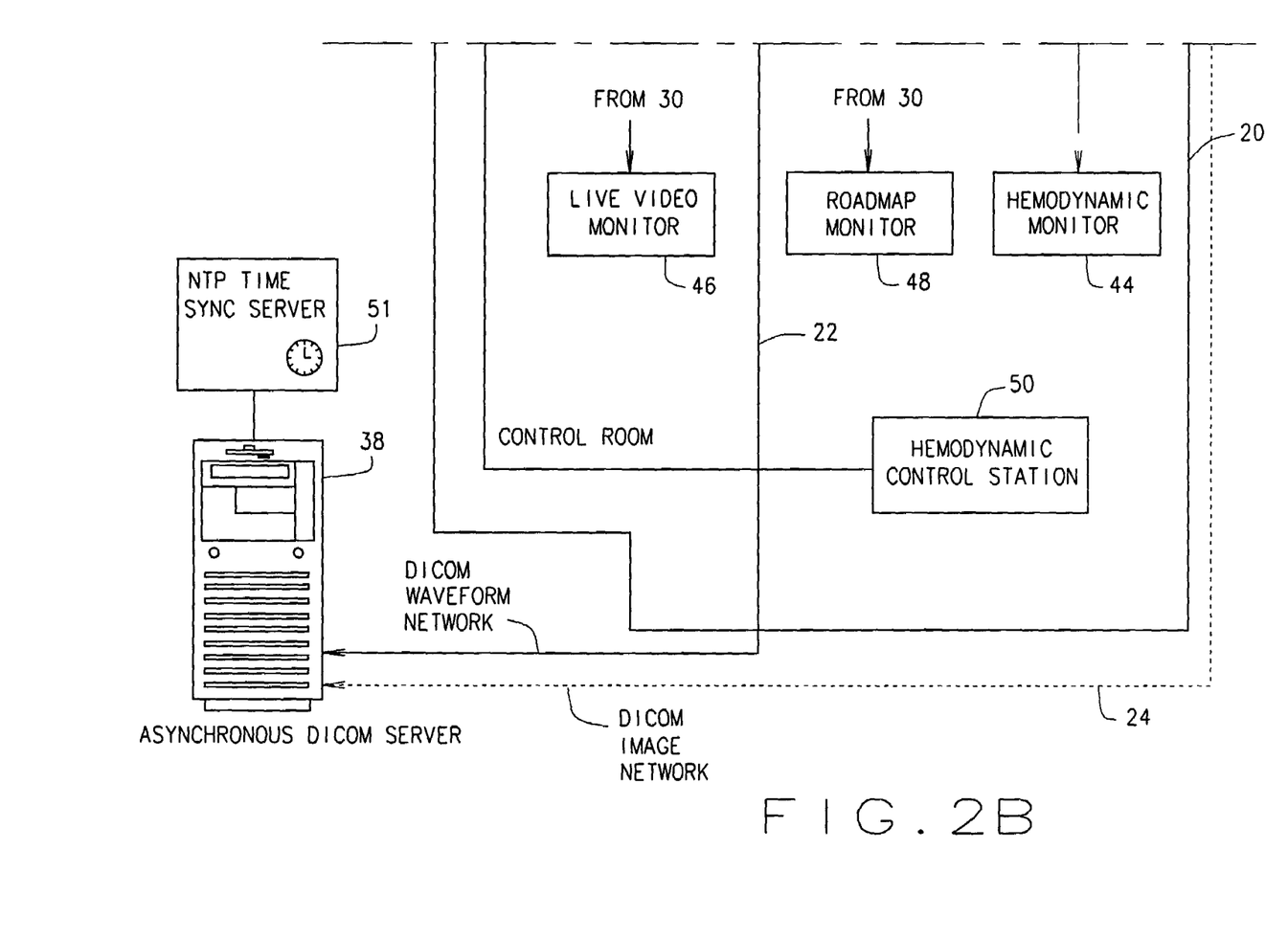

Referring now to FIG. 2, cardiac catheterization is performed on a patient 26 in a catherization laboratory 12 while patient 26 is resting on an examination table 28. After patient 26 is anesthetized, a catheter is placed in the heart of patient 26 by inserting a catheter into blood vessels in the neck, arm, or groin, and advancing the catheter through the blood vessels to the heart. The catheter is maneuvered in the heart, and a contrast agent is injected when the catheter is in position while a rapid sequence of X-ray images are recorded by X-ray imager 30. X-ray imager 30 is controlled by a technician located at X-ray control station 52. X-ray images can be viewed on live video monitors 32 and 46 located in catheterization laboratory 12 and control room 20, respectively. In an angiography procedure that provides a roadmap of blood vessels, these live X-ray images show blood flowing through the heart chambers or through blood vessels connected to the heart. A contrast-enhanced roadmap image that aids in catheter guidance is displayed on roadmap monitors 34 and 48 located in catheterization laboratory 12 and control room 20, respectively.

Each frame of imaging data acquired by X-ray imager 30 is time-stamped. The time is determined by reference to a first clock 31 located in or associated with X-ray imager 30. Each frame is later encapsulated in a DICOM object, with the time stamp associated with that frame inserted in a predetermined header field. The DICOM object from X-ray imager 30 can then be uploaded to DICOM server 38 via DICOM image network 24 for storage in a DICOM image database 19 (see FIG. 1). DICOM server 38 is programmed with database management software configured to manage the DICOM image database. The DICOM image database can reside on DICOM server 38 itself or elsewhere on another server, computer, or storage system in communication with DICOM server 38.

Cardiac catheterization laboratory 12 also houses a hemodynamic monitoring system 40, for example, a MacLab 7000 system manufactured and sold by GE Medical Systems Information Technologies, Inc., Milwaukee, Wis. This system is operated by a technician who is seated at a hemodynamic control station 50 in control room 20. During catheterization procedures, the patient undergoes physiological monitoring. Hemodynamic monitoring system 40 records physiologic data, including ECG waveforms acquired from electrodes placed on the patient. Data acquired by hemodynamic monitoring system 40 is displayed on hemodynamic monitors 42 and 44 located in catheterization laboratory 12 and control room 20, respectively. Hemodynamic monitoring system 40 is also programmed to perform ECG analysis, producing signals (i.e., "pointers") that indicate features of the ECG waveform, such as exact diastolic and systolic heart beats. Hemodynamic monitoring system 40 can also automatically acquire and display 12-lead ECGs, continuous ST segment analysis, respiration rate, thermodilution cardiac output, $SpO_2$ level, noninvasive blood pressure, and up to four invasive pressures.

Hemodynamic monitoring system 40 also maintains a catheter laboratory event log ("cath lab event log") in which the various procedures being performed are recorded. The hemodynamic technician controls all information in the cath lab event log. This technician has his or her hands free while watching and listening to the entire catheter laboratory procedure behind leaded glass. The technician enters the projection being shot and the artery selected for live video imaging into the cath lab event log before the injection of dye.

The pointers indicative of features of the ECG waveform are time-stamped by hemodynamic monitoring system 40 utilizing a second local clock 41 located in or associated with hemodynamic monitoring system 40. The time-stamped ECG waveforms are later encapsulated in DICOM objects with the associated time stamps in predetermined header fields. These DICOM objects are uploaded to DICOM server 38 via DICOM waveform network 22.

Quantitative imaging analysis is performed on acquired X-ray images using software modules resident on X-ray control station 52, on hemodynamic control station 50 or on any physician review workstation capable of communicating with DICOM server 38, such as station 14 represented in FIG. 1. Such analysis requires the selection of images acquired substantially in synchronization with certain cardiac events of interest. This selection could be accomplished by selecting frames of imaging data having a time stamp closest in time to time-stamped pointers corresponding to particular cardiac events. However, first clock 31 and second clock 41 must be synchronized to avoid time offset differences (or, synonymously, "offsets"). Such offsets may be significant and may change in magnitude over time.

To synchronize first clock 31 and second clock 41, a Network Time Protocol (NTP) time synchronization server software module 51 resides in DICOM server 38. In addition, data acquisition systems 30 and 40 and clocks 31 and 41, respectively, are also each provided with respective NTP time synchronization that synchronize clocks 31 and 41 of data acquisition systems 30 and 40. Each NTP time synchronization client software module initiates a time request exchange with the NTP time synchronization server software module 51. As a result of this exchange, the client is able to calculate the link delay, its local offset, and adjust its local clock to match a reference clock at another computer (e.g., DICOM server 38) where server module 51 resides. NTP time synchronization modules for clocks 31 and 41 also update their respective clocks (for example, at regular one minute intervals) to ensure that they do not drift significantly from synchronization.

Accordingly, frames of imaging data acquired by X-ray imager 30 can be synchronized with features in the physiological data acquired by hemodynamic monitoring system 40 that represent predetermined cardiac events of interest. For example, frames of imaging data representing a succession of images of a patient's heart during a study are acquired using imager 30. Imager 30 is programmed to time stamp each acquired frame with the a time stamp utilizing clock 31. Imager 30 is also programmed to determine respective offsets of clock 31 relative to a reference clock such using, for example, NTP client time synchronization module for clock 31 and NTP time synchronization server software module 51. Acquired frames and time stamps and local offsets associated with the acquired frames are uploaded to DICOM server 38 via DICOM image network 24. This data is transmitted in the format of DICOM objects, each DICOM object encapsulating a respective frame of imaging data and having a header comprising respective fields for a time stamp and an offset associated with that frame.

During the same study, physiologic data is acquired from the patient using hemodynamic monitoring system 40. Hemodynamic monitoring system 40 is programmed to time stamp acquired physiologic data corresponding to one or more predetermined cardiac events. The time stamps are generated utilizing clock 41. Hemodynamic monitoring system 40 is also programmed to determine offsets of clock 41 relative to the reference clock used by NTP time synchronization server 51 for each time stamp associated with the physiologic data. The acquired physiologic data with associated time stamps and local offsets are uploaded to DICOM server 38 via DICOM waveform network 22. This data is transmitted in the format of DICOM objects, each of which encapsulates physiologic data and which includes a header comprising fields for a time stamp and an offset associated with that physiologic data.

DICOM server 38 executes a database management software module that instructs DICOM server 38 to store imaging and physiologic DICOM objects in a database (not shown in FIG. 2). This database management software module also instructs DICOM server 38 to respond to requests for files from remote workstations. In particular, DICOM server 38 can be requested to send a set of DICOM files to a physician review station for quantitative imaging analysis. A quantitative analysis software module can be resident, for example, on x-ray control station 52, hemodynamic control station 50 or physician review station 14 (see FIGS. 1 and 2). The quantitative analysis software module interprets time stamps and local offsets in DICOM object headers and merges images with physiologic data (e.g., ECG waveforms) for automatic image selection. For example, in one configuration, when a physician replays images, all diastole frames and matching systole frames are displayed. The displayed frames are selectable for left ventricular analysis. Individual frames for stenosis evaluation are identified as to their contractility in the DICOM header. The quantitative analysis software module allows a physician to select an individual frame for quantitative coronary analysis (QCA) with an indicator to indicate whether or not it is at the peak when the physician selects a QCA tool. The physician may then frame forward or backward until both the required position and contractility is attained.

In some configurations, review station 14 is a cardiology analysis system having an operator interface, a display monitor and a computer. The computer is programmed to compensate for unsynchronized local clocks of imager 30 and hemodynamic monitoring system 40. Compensation is accomplished using the associated local offsets when time stamps of frames of imaging data are compared to time stamps of physiological data corresponding to cardiac events of interest. More particularly, to obtain the true times of data acquisition relative to the reference clock used by NTP time synchronization server 51, the computer is programmed to adjust the time stamps by the amount of offset before the time stamps are compared. In this manner, the quantitative imaging analysis software module is able to select a frame that was acquired substantially in synchronization with the occurrence of a predetermined cardiac event recorded in the physiological data for the study in issue. The selected frame of imaging data is then utilized for quantitative coronary analysis. For example, two frames corresponding to the diastole and systole of a particular cardiac cycle are selected and then analyzed for left ventricular analysis.

In yet another configuration, local clocks 31 and 41 at imager 30 and hemodynamic monitoring system 40, respectively, are synchronized with the reference clock used by NTP time synchronization server 51 in real-time using NTP time synchronization. By "real time," it is meant that clocks 31 and 41 are adjusted so that their time stamps represent adjusted, i.e., synchronized, time. In this configuration, the header of each DICOM object has a field containing the adjusted time stamp, so that a local offset field is not required.

Configurations of the present invention are not limited to using NTP. Other distributed network time protocols that are used in various configurations include, for example, Simple Network Time Protocol ("SNTP"), Experimental Network Time Protocol ("XNTP"), Secure Network Time Protocol ("STIME"), and Real-Time Transport Protocol ("RTP").

Figure 3:
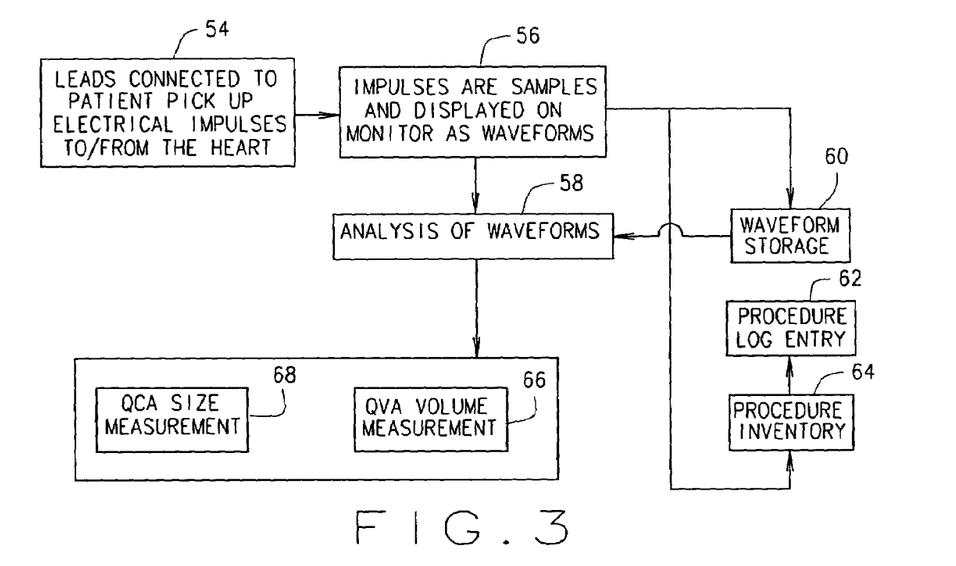
FIG. 3 is a flowchart indicating data acquisition by the hemodynamic monitoring system depicted in FIG. 2.

FIG. 3 is a flowchart representing a physiological monitoring process that is performed in catheterization laboratory 12 in some configurations of the present invention. Leads connected to a patient undergoing the procedure pick up electrical pulses to and from the patient's heart at 54. The waveforms of the electrical pulses are sampled and displayed on a monitor as waveforms at 56 and stored in a computer memory at 60. Hemodynamic monitoring system 40 is programmed to perform ECG analysis of waveforms at 58, results of which are also stored in the computer memory. As part of that analysis, hemodynamic monitoring system 40 is programmed to time stamp pointers to various characteristic features in the acquired waveforms. Optionally, quantitative analysis (QVA volume measurement 66 or QCA size measurement 68) can be performed at hemodynamic control station 50. QCA and QVA software modules may be included as part of hemodynamic monitoring system 40, or one or both of these software modules may reside on a PC connected to hemodynamic monitoring system 40. While the procedure is under way, a hemodynamic technician enters identifying codes and activates time stamps for various procedures being performed at 62. These procedures are maintained in a procedure log 64 called the "cath lab event log".

Figure 4:
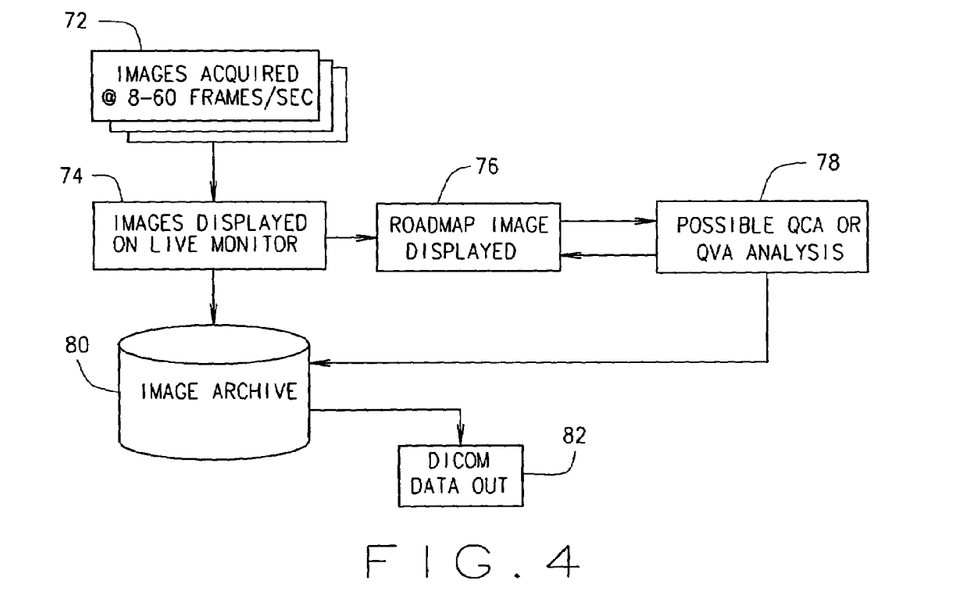
FIG. 4 is a flowchart indicating data acquisition by the x-ray imaging system depicted in FIG. 2.

In some configurations and referring to FIG. 4, various steps of the imaging process are performed in catheterization laboratory 12. X-ray images are acquired in some configurations at a frame rate of 8 to 60 frames per second at 72. Acquired images are displayed as live video at 74 on live video monitor 32 (see FIG. 2). A contrast-enhanced roadmap image is displayed at 76 on roadmap monitor 34 (see FIG. 2). The roadmap image assists a physician guiding the catheter through the patient's blood vessels and can also be used to perform quantitative image analysis (e.g., QCA or QVA) at 78. Images are time stamped and stored in an image archive 80, along with, in some configurations, results from quantitative image analysis. Image archive 80 contains the database managed by DICOM server 38 (see FIG. 2). DICOM server 38 also downloads DICOM data from image archive 80 to a requesting workstation at 82, for example via a TCP/IP network. Images can then undergo quantitative image analysis as described above.

In some configurations of the present invention, an angiographic LV (Left Ventricular) analysis is performed utilizing multiple dye-filled images at diastole and systole. An edge detection algorithm using multiple images facilitates total image edge detection of dye-filled left ventricles, providing enhanced accuracy and repeatability. In these configurations, images of the dye filled ventricle at the same phase of different cardiac cycles provide additional information than would be obtained by analyzing a single image at that phase.

Figure 5:
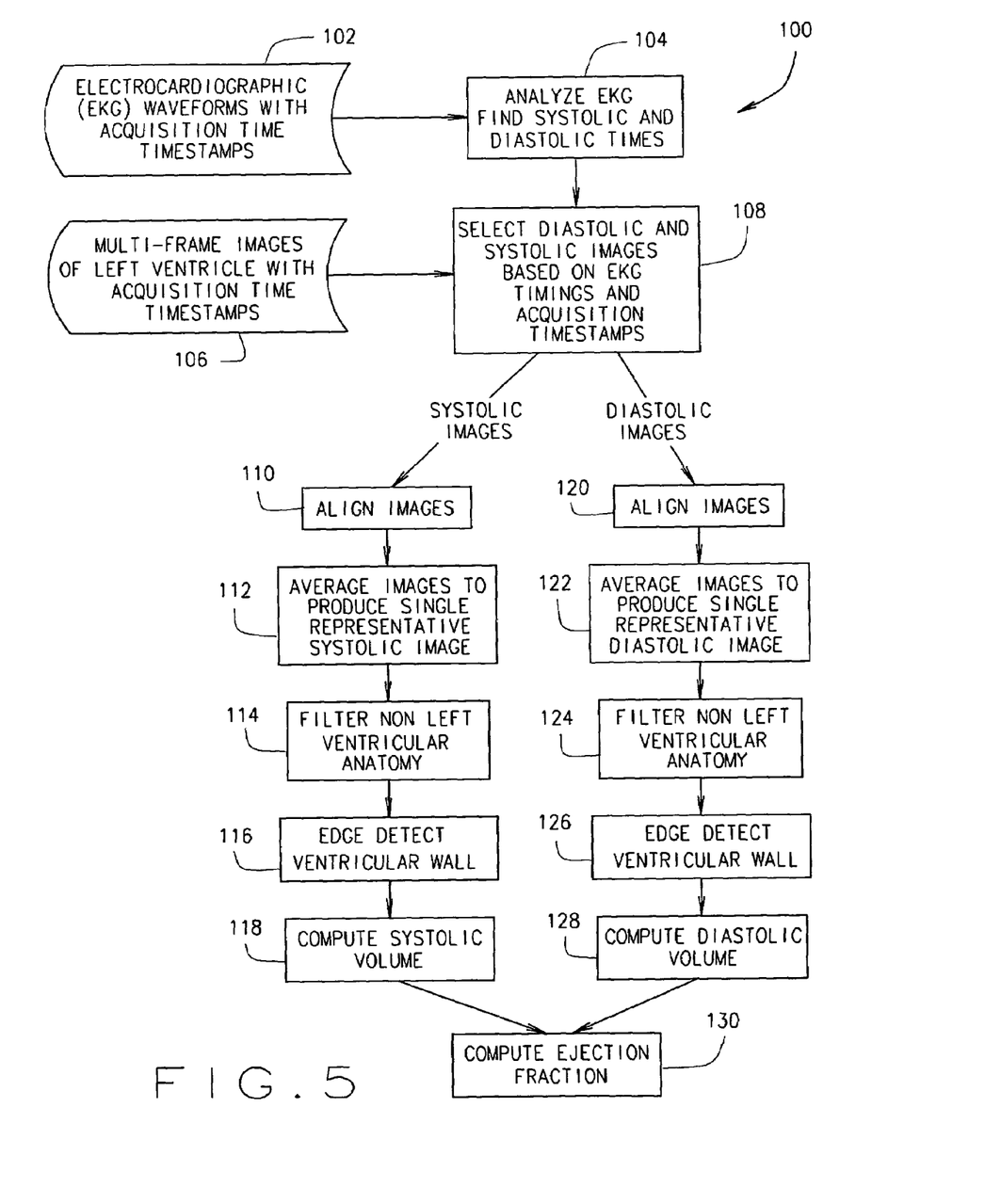
FIG. 5 is a flowchart indicating data processing by the workstation of FIG. 1.

For example, FIG. 5 is a flowchart indicating data processing by workstation 14 of FIG. 1, in which the technical effect is achieved by analyzing, from a DICOM database of a patient study, electrocardiograph (ECG or synonymously, EKG) waveforms with acquisition time stamps 102 to find systolic and diastolic times at 104. Also from the DICOM database of the patient study, image frames of the left ventricle 106 are selected at 108. The selected images are diastolic and systolic images based on ECG images and acquisition timestamps. More particularly, images from two or more cardiac cycles are selected at 108, so that there are two or more times and frames for both phases.

For the plurality of selected systolic images, the images are aligned with one another at 110 utilizing a alignment software module and averaged at 112 utilizing an averaging software module to produce a single representative systolic image. (An "image," as that term is used in FIG. 5 and in connection therewith, more accurately refers to a digital representation of an image.) Portions of the image that do not represent left ventricular anatomy are filtered out or removed from the single image at 114 utilizing a filtering software module. The edge of the ventricular wall is then detected at 116 utilizing an edge detection software module, and a systolic volume is determined at 118 from the detected edge utilizing a volume-determining software module. A corresponding sequence of operations 120, 122, 124, 126, and 128 is also performed on diastolic images to determine a diastolic volume. From both the determined diastolic volume and the determined systolic volume, some configurations of the present invention determine an ejection fraction utilizing an ejection fraction determining software module.

Thus, some configurations of the present invention provide a method for analyzing stored frames of time-stamped imaging data 106 and time-stamped physiologic data 102 obtained during a study of a patient during a plurality of cardiac cycles. The physiologic data may be ECG waveform data, pressure measurements, or other data. A computer, such as workstation 14, is used to analyze 104 the stored physiologic data 102 to determine time of a selected phase of the plurality of cardiac cycles. The stored data in some configurations is X-ray imaging data, which may have been enhanced by injection of a contrast agent into the cardiovascular system of patient 28. Computer 14 is also used to select 108, in the plurality of cardiac cycles, stored images 106 corresponding to the determined times of the selected phase and to align 110 and average 112 images corresponding to the selected phase across the plurality of cardiac cycles to produce a single representative frame of image data.

In some configurations, computer or workstation 14 is further used to filter 114 non-left ventricle anatomy from the single representative frame of image data. Also in some configurations, computer or workstation 14 is used to detect 116 edges of a left ventricle wall in the filtered, single representative frame of image data, and is further used in some configurations to determine 118 cardiac volume in the filtered, single representative frame of image data.

In some configurations, the selected cardiac phase is a systolic phase, and the determined cardiac volume is a systolic volume. In various other configurations, the selected cardiac phase is a diastolic phase and the determined cardiac volume is a diastolic volume. In still other configurations, both a selected systolic phase and a selected diastolic phase are processed to determine both a systolic volume and a diastolic volume, and computer 14 is used to determine an ejection fraction utilizing the determined systolic volume and the determined diastolic volume.

Some configurations of the present invention provide a computer or workstation 14 configured to analyze the stored physiologic data to determine times of a selected phase in the plurality of cardiac cycles. The computer is further configured to perform all or some subset of the various processes and procedures described above.

Configurations of the present invention are useful in applications other than cardiac imaging. For example, some configurations utilize time-stamped cyclical waveform data having recognizable phases along with a plurality of related cycles of time-stamped cyclical image data collected during a study of an object. In these configurations, the time-stamped cyclical waveform data is used in much the same way as the EKG or ECG waveform data, except that systolic and/or diastolic phases are replaced by other phases appropriate to the intended application. Also, images for the intended application other than those of a patient's heart are used. In these applications, images corresponding to a selected phase in different cycles are averaged to produce a single image representative of the object being imaged at the selected cycle. Filtering may also be performed that corresponds to non-left ventricular anatomy filtering in a cardiac application, and edge detection suitable for the application may also be performed. If the object being imaged is a pumping apparatus, volumes at two phases can be determined analogously to the determination of the systolic and diastolic volumes, and an ejection fraction (or corresponding measure) may be determined.

It will thus be appreciated that various configurations of the present invention provide fully automatic left ventricle analysis using multiple images of systole and diastole. Using these multiple images, a single representative image of each phase proves more accurate and repeatable edge detection and dependent measures, such as ejection fraction than is known in current methods and apparatus. Corresponding advantages can be obtained in configurations of the present invention in other applications, including non-medical applications in which various forms of cyclical data and images of an object are recorded.

While the invention has been described in terms of various specific embodiments, those skilled in the art will recognize that the invention can be practiced with modification within the spirit and scope of the claims.

What is claimed is:

1. A method utilizing a computer in communication with an imaging system and a monitoring system for analyzing stored frames of time-stamped imaging data and time-stamped physiologic data obtained during a study of a patient during a plurality of cardiac cycles, the imaging data comprising frames representative of a succession of images of the patient's heart, said method comprising:

time-stamping each of the frames of the imaging data acquired by said computer using a first clock within the imaging system;

time-stamping at least one feature within the physiologic data using a second clock within the monitoring system, the second clock different than the first clock;

storing the time-stamped frames of the imaging data and the time-stamped physiologic data within a memory device;

synchronizing time-stamps generated by the first clock with time-stamps generated by the second clock by comparing the first clock and the second clock to a reference clock within the memory device;

analyzing the stored time-stamped physiologic data to determine times of a selected phase in the plurality of cardiac cycles;

selecting, in the plurality of cardiac cycles, the stored time-stamped frames of imaging data corresponding to the determined times of the selected phase;

aligning and averaging the selected frames of imaging data corresponding to the selected phase across the plurality of cardiac cycles; and producing a single representative frame of image data based on the aligned and averaged frames of imaging data.

2. A method in accordance with claim 1 further comprising utilizing the computer to filter non-left ventricle anatomy from the single representative frame of image data.

3. A method in accordance with claim 2 further comprising utilizing the computer to detect edges of a left ventricle wall in the filtered, single representative frame of image data.

4. A method in accordance with claim 3 further comprising utilizing the computer to determine cardiac volume utilizing said filtered, single representative frame of image data.

5. A method in accordance with claim 4 wherein said selected cardiac phase is a systolic phase and said determined cardiac volume is a systolic volume.

6. A method in accordance with claim 4 wherein said selected cardiac phase is a diastolic phase and said determined cardiac volume is a diastolic volume.

7. A method wherein the method of claim 4 is performed for both a selected systolic phase and a selected diastolic phase to determine both a systolic volume and a diastolic volume, and further comprising utilizing the computer to determine an ejection fraction utilizing said determined systolic volume and said determined diastolic volume.

8. A method in accordance with claim 1 wherein the physiologic data comprises ECG waveform data.

9. A method in accordance with claim 1 wherein said imaging data comprises X-ray imaging data.

10. A method in accordance with claim 9 wherein the X-ray imaging data comprises data enhanced by injection of a contrast agent into the cardiovascular system of the patient.

11. A method in accordance with claim 1 wherein synchronizing time-stamps generated by the first clock with time-stamps generated by the second clock further comprises calculating at least one of a link delay and a local offset, the local offset calculated with respect to the reference clock and one of the first clock and the second clock.

12. A cardiology analysis apparatus for analyzing stored frames of time-stamped imaging data and time-stamped physiologic data obtained during a study of a patient during a plurality of cardiac cycles, the imaging data comprising frames representative of a succession of images of the patient's heart, said apparatus comprising:

an imaging system;

a monitoring system; and a computer in communication with said imaging system and said monitoring system, said computer configured to:

time-stamp each of the frames of the imaging data acquired by said apparatus using a first clock within said imaging system;

time-stamp at least one feature within the physiologic data using a second clock within said monitoring system, the second clock different than the first clock;

store the time-stamped frames of the imaging data and the time-stamped physiologic data within a memory device;

synchronize time-stamps generated by the first clock with time-stamps generated by the second clock by comparing the first clock and the second clock to a reference clock within the memory device;

analyze the stored time-stamped physiologic data to determine times of a selected phase in the plurality of cardiac cycles;

select, in the plurality of cardiac cycles, the stored time-stamped frames of imaging data corresponding to the determined times of the selected phase;

align and average the selected frames of imaging data corresponding to the selected phase across the plurality of cardiac cycles; and produce a single representative frame of image data based on the aligned and averaged frames of imaging data.

13. An apparatus in accordance with claim 12 wherein said computer is further configured to filter non-left ventricle anatomy from the single representative frame of image data.

14. An apparatus in accordance with claim 13 wherein said computer is further configured to detect edges of a left ventricle wall in the filtered, single representative frame of image data.

15. An apparatus in accordance with claim 14 wherein said computer is further configured to determine cardiac volume utilizing said filtered, single representative frame of image data.

16. An apparatus in accordance with claim 15 wherein said selected cardiac phase is a systolic phase and said determined cardiac volume is a systolic volume.

17. An apparatus in accordance with claim 15 wherein said selected cardiac phase is a diastolic phase and said determined cardiac volume is a diastolic volume.

18. An apparatus in accordance with claim 15 wherein for both a selected systolic phase and a selected diastolic phase, said computer is configured to determine both a systolic volume and a diastolic volume, and said computer is further configured to determine an ejection fraction utilizing said determined systolic volume and said determined diastolic volume.

19. An apparatus in accordance with claim 12 wherein said computer is configured to:

calculate a first offset between the first clock and the reference clock; and calculate a second offset between the second clock and the reference clock.

20. An apparatus in accordance with claim 19 wherein said computer is configured to:

adjust the time-stamps generated by the first clock based on the first offset; and adjust the time-stamps generated by the second clock based on the second offset.

21. An apparatus in accordance with claim 19 wherein said computer is configured to merge the time-stamped imaging data with the time-stamped physiological data based on the time-stamps generated by the first clock, the time-stamps generated by the second clock, the first offset, and the second offset.

22. A method utilizing a computer in communication with an imaging system and a monitoring system for analyzing stored frames of time-stamped cyclical image data obtained during a study of an object during a plurality of cycles, said method comprising:

time-stamping at least one frame within the cyclical image data acquired by said computer using a first clock within the imaging system;

time-stamping at least one feature within physiologic data acquired by said computer using a second clock within the monitoring system, the second clock different than the first clock;

storing the time-stamped cyclical image data and the time-stamped physiologic data within a memory device;

synchronizing time-stamps generated by the first clock with time-stamps generated by the second clock by comparing the first clock and the second clock to a reference clock within the memory device;

analyzing the stored time-stamped cyclical image data to determine time of a selected phase of the cycle;

selecting, in the plurality of cycles of time-stamped cyclical image data, stored images corresponding to the determined times of the selected phase;

aligning and averaging the selected images corresponding to the selected phase across the plurality of cycles; and producing a single representative frame of image data based on the aligned and averaged frames of imaging data.

23. An analysis apparatus for analyzing stored frames of time-stamped cyclical imaging data and time-stamped waveform data obtained during a study of an object during a plurality of cycles, the imaging data comprising frames representative of a succession of images of the object, said apparatus comprising:

an imaging system;

a monitoring system; and a computer in communication with said imaging system and said monitoring system, said computer configured to:

time-stamp each of the frames within the cyclical image data acquired by said apparatus using a first clock within said imaging system;

time-stamp at least one feature within the waveform data using a second clock within said monitoring system, the second clock different than the first clock;

store the time-stamped frames of the cyclical image data and the time-stamped waveform data in a memory device;

synchronize time-stamps generated by the first clock with time-stamps generated by the second clock by comparing the first clock and the second clock to a reference clock within the memory device;

analyze the stored time-stamped waveform data to determine times of a selected phase in the plurality of cycles;

select, in the plurality of cycles, stored frames of time-stamped cyclical imaging data corresponding to the determined times of the selected phase;

align and average the selected frames of imaging data corresponding to the selected phase across the plurality of cycles; and produce a single representative frame of image data using the aligned and averaged frames of imaging data.

* * * * *